(12) United States Patent
Hsu et al.

(10) Patent No.: US 10,100,410 B2
(45) Date of Patent: Oct. 16, 2018

(54) FILM THICKNESS MONITORING SYSTEM AND METHOD USING THE SAME

(71) Applicant: Industrial Technology Research Institute, Hsinchu (TW)

(72) Inventors: Yu-Lin Hsu, Tainan (TW); Kuo-Hsin Huang, Hsinchu County (TW); Chien-Hung Lin, Changhua County (TW); Pang-Min Shih, Hsinchu (TW); Chao-Feng Sung, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 22 days.

(21) Appl. No.: 15/229,136

(22) Filed: Aug. 5, 2016

(65) Prior Publication Data

US 2018/0037996 A1 Feb. 8, 2018

(51) Int. Cl.
 C23C 16/52 (2006.01)
 C23C 14/54 (2006.01)
 G01N 29/12 (2006.01)

(52) U.S. Cl.
 CPC .............. C23C 16/52 (2013.01); C23C 14/54 (2013.01); C23C 14/546 (2013.01); G01N 29/12 (2013.01); G01N 2291/0237 (2013.01); G01N 2291/0256 (2013.01); G01N 2291/02854 (2013.01); G01N 2291/2697 (2013.01)

(58) Field of Classification Search
 CPC ..................................... C23C 6/52; C23C 6/54
 See application file for complete search history.

(56) References Cited

U.S. PATENT DOCUMENTS

| 4,588,942 A * | 5/1986 | Kitahara .............. C23C 14/546 |
| | | 204/298.03 |
| 5,536,317 A | 7/1996 | Crain et al. |
| 8,718,956 B2 | 5/2014 | Hesketh et al. |
| (Continued) | | |

FOREIGN PATENT DOCUMENTS

| CN | 1458297 | 11/2003 |
| CN | 102232180 | 11/2011 |
| (Continued) | | |

OTHER PUBLICATIONS

"Notice of Allowance of Taiwan Counterpart Application," dated Sep. 26, 2017, p. 1-p. 4.

Primary Examiner — Joseph A Miller, Jr.
(74) Attorney, Agent, or Firm — JCIPRNET

(57) ABSTRACT

A film thickness monitoring system is provided. The film thickness monitoring system includes a source, a valve, and a chamber. The source is configured to provide a deposition material. The valve is connected to the source. The chamber includes a manifold, a quartz crystal microbalance, and a pressure sensor. The manifold is connected to the valve and has at least one first nozzle and at least one second nozzle. The quartz crystal microbalance is disposed opposite to the at least one second nozzle. The deposition material is adapted to be deposited on the quartz crystal microbalance through the at least one second nozzle, and the quartz crystal microbalance includes a shutter facing the at least one second nozzle. The pressure sensor is disposed in the manifold. A method for monitoring a film thickness deposition process is also provided.

13 Claims, 6 Drawing Sheets

(56) References Cited

U.S. PATENT DOCUMENTS

| | | | |
|---|---|---|---|
| 2002/0074225 A1* | 6/2002 | Shi | C23C 14/352 204/298.09 |
| 2006/0144335 A1* | 7/2006 | Lee | C23C 14/505 118/719 |
| 2008/0095694 A1* | 4/2008 | Nakayama | B82L 31/00 423/445 B |
| 2011/0165320 A1* | 7/2011 | Choi | C23C 14/12 427/66 |
| 2012/0009706 A1* | 1/2012 | Choi | C23C 14/044 438/34 |
| 2012/0114833 A1* | 5/2012 | Nakagawa | C23C 14/24 427/8 |
| 2014/0053779 A1 | 2/2014 | Martinson et al. | |
| 2014/0127833 A1* | 5/2014 | Kim | C23C 16/52 438/5 |

FOREIGN PATENT DOCUMENTS

| | | |
|---|---|---|
| CN | 103080365 | 5/2013 |
| CN | 104087908 | 10/2014 |
| JP | 2008122200 | 5/2008 |
| TW | 201311924 | 3/2013 |
| WO | 2015182090 | 12/2015 |

\* cited by examiner

FILM THICKNESS MONITORING SYSTEM AND METHOD USING THE SAME

TECHNICAL FIELD

The technical field relates to a film thickness monitoring system and method using the same.

BACKGROUND

Deposition methods are widely used in forming specific electronic devices. For example, chemical vapor deposition or physical vapor deposition are conventional deposition methods used to form different devices. The deposition processes form thin films ranging from one atom up to millimeters. Multiple layers of different materials can be used.

When forming the thin films, the thickness of the films and the deposition rate need to be precise. Thus, it is essential for the thickness of the films to be able to be monitored during the deposition processes. This way, the deposition of the thin film is accurate according to the requirements of the structure that is formed.

SUMMARY

An exemplary embodiment of the disclosure provides a film thickness monitoring system. The film thickness monitoring system includes a source, a valve, and a chamber. The source is configured to provide a deposition material. The valve is connected to the source. The chamber includes a manifold, a quartz crystal microbalance, and a pressure sensor. The manifold is connected to the valve and has at least one first nozzle and at least one second nozzle. The quartz crystal microbalance is disposed opposite to the at least one second nozzle. The deposition material is adapted to be deposited on the quartz crystal microbalance through the at least one second nozzle, and the quartz crystal microbalance includes a shutter facing the at least one second nozzle. The pressure sensor is disposed in the manifold.

An exemplary embodiment of the disclosure provides a chamber adapted for a film thickness monitoring system. The chamber includes a manifold, a quartz crystal microbalance, and a pressure sensor. The manifold has at least one first nozzle and at least one second nozzle. The quartz crystal microbalance is disposed opposite to the at least one second nozzle. The deposition material is adapted to be deposited on the quartz crystal microbalance through the at least one second nozzle, and the quartz crystal microbalance includes a shutter facing the at least one second nozzle. The pressure sensor is disposed in the manifold.

An exemplary embodiment of the disclosure provides a method for monitoring a film thickness deposition process. The method includes the following steps. A deposition material is deposited on a target through at least one first nozzle of a manifold and on a quartz crystal microbalance through at least one second nozzle of the manifold. Next, a thickness of the deposition material on the target is measured through the quartz crystal microbalance, and a pressure sensor disposed in the manifold is calibrated to measure the thickness of the deposition material with reference to the quartz crystal microbalance. Next, a shutter of the quartz crystal microbalance facing the at least one second nozzle is closed through a shutter controller after the pressure sensor is calibrated, and the thickness of the deposition material on the target is continued to be measured through the pressure sensor.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1:
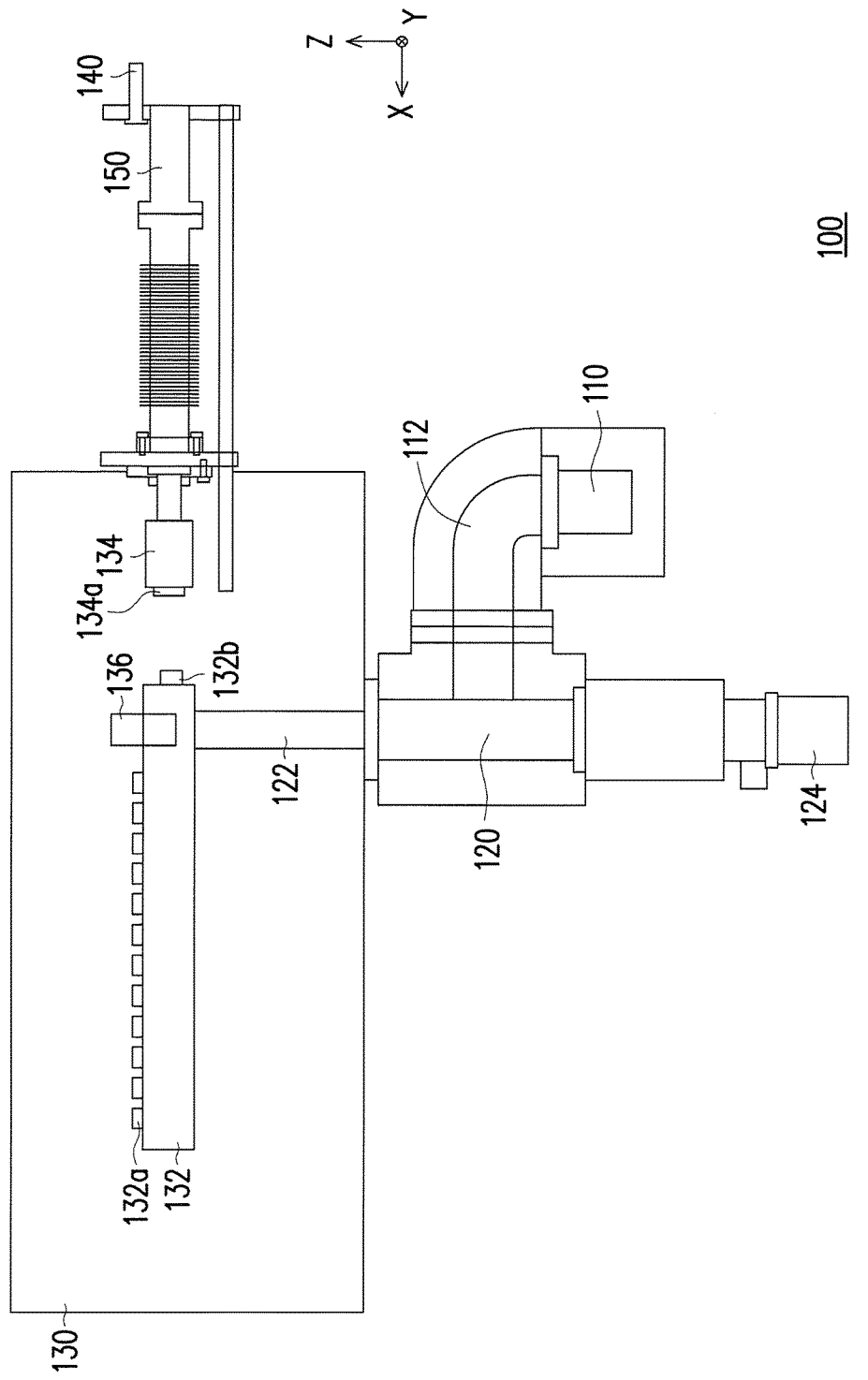
FIG. 1 is a schematic diagram illustrating a film thickness monitoring system, according to an exemplary embodiment.
Figure 2:
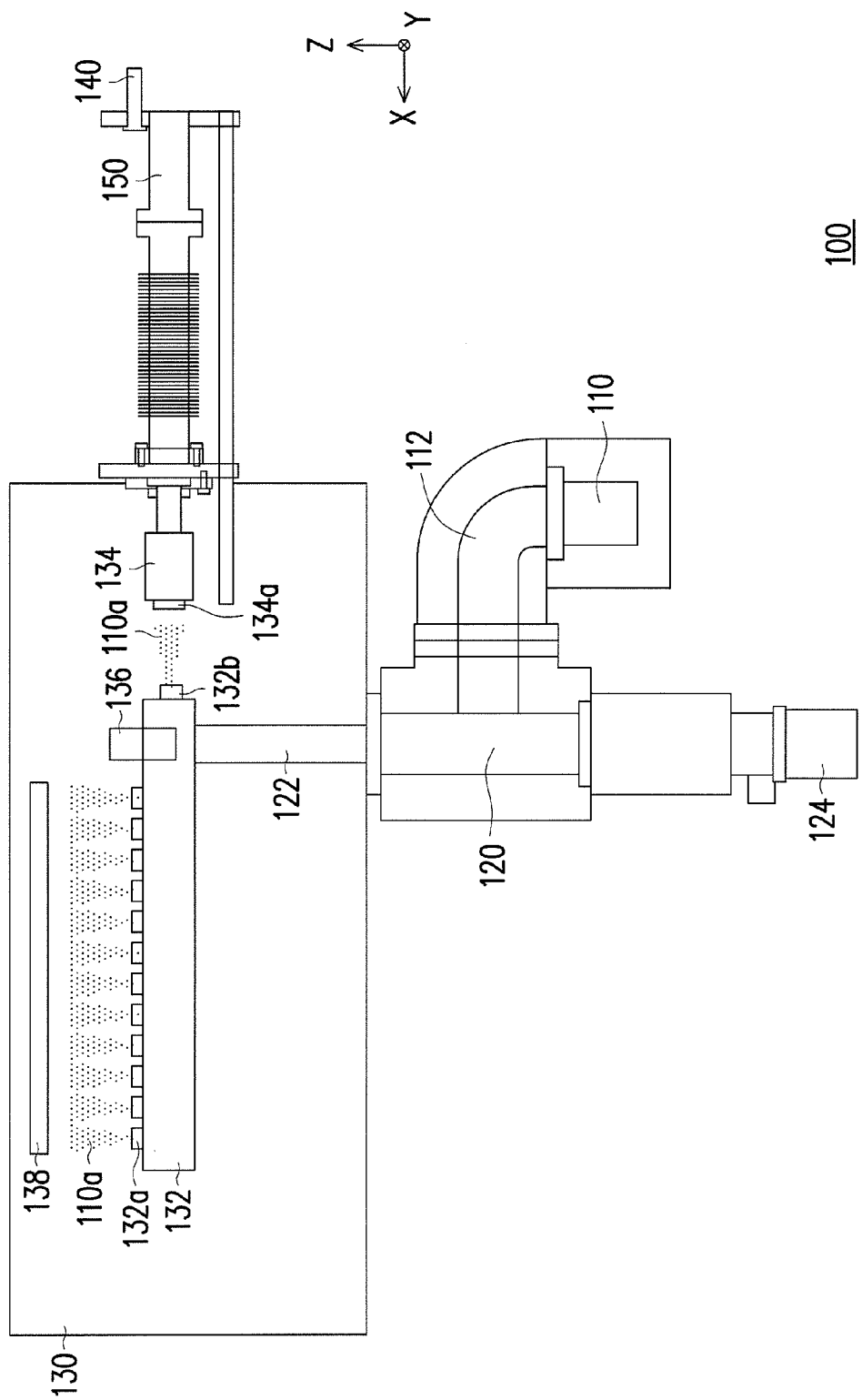
FIG. 2 is a schematic diagram illustrating the film thickness monitoring system of FIG. 1 monitoring a deposition process.

FIG. 1 is a schematic diagram illustrating a film thickness monitoring system, according to an exemplary embodiment. FIG. 2 is a schematic diagram illustrating the film thickness monitoring system of FIG. 1 monitoring a deposition process. Referring to FIG. 1 and FIG. 2, a film thickness monitoring system 100 includes a source 110, a valve 120, and a chamber 130. The source 110 is configured to provide a deposition material 110a (shown in FIG. 2). Specifically, the deposition material 110a is adapted to be in the source 110. In the embodiment, the deposition material 110a is anything that the user requires to deposit. That is to say, the deposition material 110a is organic or inorganic material. In the embodiment, the source 110 is a crucible adapted to be heated so as to vaporize the deposition material 110a. The valve 120 is connected to the source 110. In the embodiment, the valve 120 is connected to the source 110 through an L-pipe 112. However, the disclosure is not limited thereto. The valve 120 is connected to the source 110 through pipes or transfer tubes in any suitable method.

In the embodiment, the chamber 130 includes a manifold 132, a quartz crystal microbalance (QCM) 134, and a pressure sensor 136. The manifold 132 is connected to the valve 120 and has at least one first nozzle 132a and at least one second nozzle 132b. In particular, the valve 120 is connected to the manifold 132 through a transfer tube 122. In the embodiment, there are a plurality of first nozzles 132a and one second nozzle 132b. However, the disclosure is not limited thereto, and the number of first nozzles 132a and the number of second nozzles 132b may be adjusted according to user requirements. In the embodiment, the first nozzles 132a and the second nozzle 132b are disposed on different sides of the manifold 132. The QCM 134 is disposed opposite to the second nozzle 132b. The deposition material 110a is adapted to be deposited on the QCM 134 through the second nozzle 132b, and the QCM 134 includes a shutter 134a facing the second nozzle 132b. However, the disclosure is not limited thereto. In other embodiments, the first and second nozzles 132a, 132b may also be on the same side of the manifold 132 if required by the user.

In the embodiment, the film thickness monitoring system 100 includes a shutter controller 140. The shutter controller 140 is configured to control the shutter 134a on the QCM 134 to open or close. In addition, the film thickness monitoring system 100 includes a supporter 150, for supporting the QCM 134. The supporter 150 is configured to adjust a position of the QCM 134 with respect to the second nozzle 132b. In the embodiment, the supporter 150 adjusts the position of the QCM 134 in the x-direction. However, the disclosure is not limited thereto, and the supporter 150 may also adjust the position of the QCM 134 in the y-direction or the z-direction according to user requirements.

In the embodiment, referring to FIG. 2, when the film thickness monitoring system 100 is monitoring a deposition process, the chamber further includes a target 138. The target 138 is disposed opposite to the first nozzles 132a. As seen in FIG. 2, the deposition material 110a is deposited on the target 138 through the first nozzles 132a during the deposition process. Also as seen in FIG. 2, during the monitoring of the deposition process, the deposition material 110a is deposited on the QCM 134. The target 138 is, for example, a substrate for the deposition material 110a to be deposited on. In the embodiment, when the deposition process is being performed, the target 138 is not disposed in the chamber 130. During the deposition process, the target 138 is disposed in the chamber 130 to be deposited on. However, the disclosure is not limited thereto. The target 138 may be a structure adapted to hold a substrate to be deposited on, and may be in the chamber 130 even when the deposition process is not being performed. Or, the target 138 is deposited on and may still be in the chamber 130 when the deposition process is not being performed. The configuration of the target 138 may be determined according to user requirements.

In the embodiment, the chamber 130 is adapted to be a vacuum chamber. Specifically, during the deposition process, the deposition process is performed in the vacuum chamber 130. Furthermore, a pressure in the manifold 132 is substantially the same as a pressure at the target 138 in the vacuum chamber 130. This way, the pressure sensor 136 detecting the pressure in the manifold 132 detects substantially the same pressure at the target 138. As a result, the results from the pressure sensor 136 may be used to calculate the film thickness and deposition rate of the deposition material 110a. In addition, the valve 120 and the source 110 are disposed outside the chamber 130. However, the valve 120 and the source 110 are connected to the chamber 130 so that the interior of the valve 120 and the source 110 are part of the vacuum.

Figure 3:
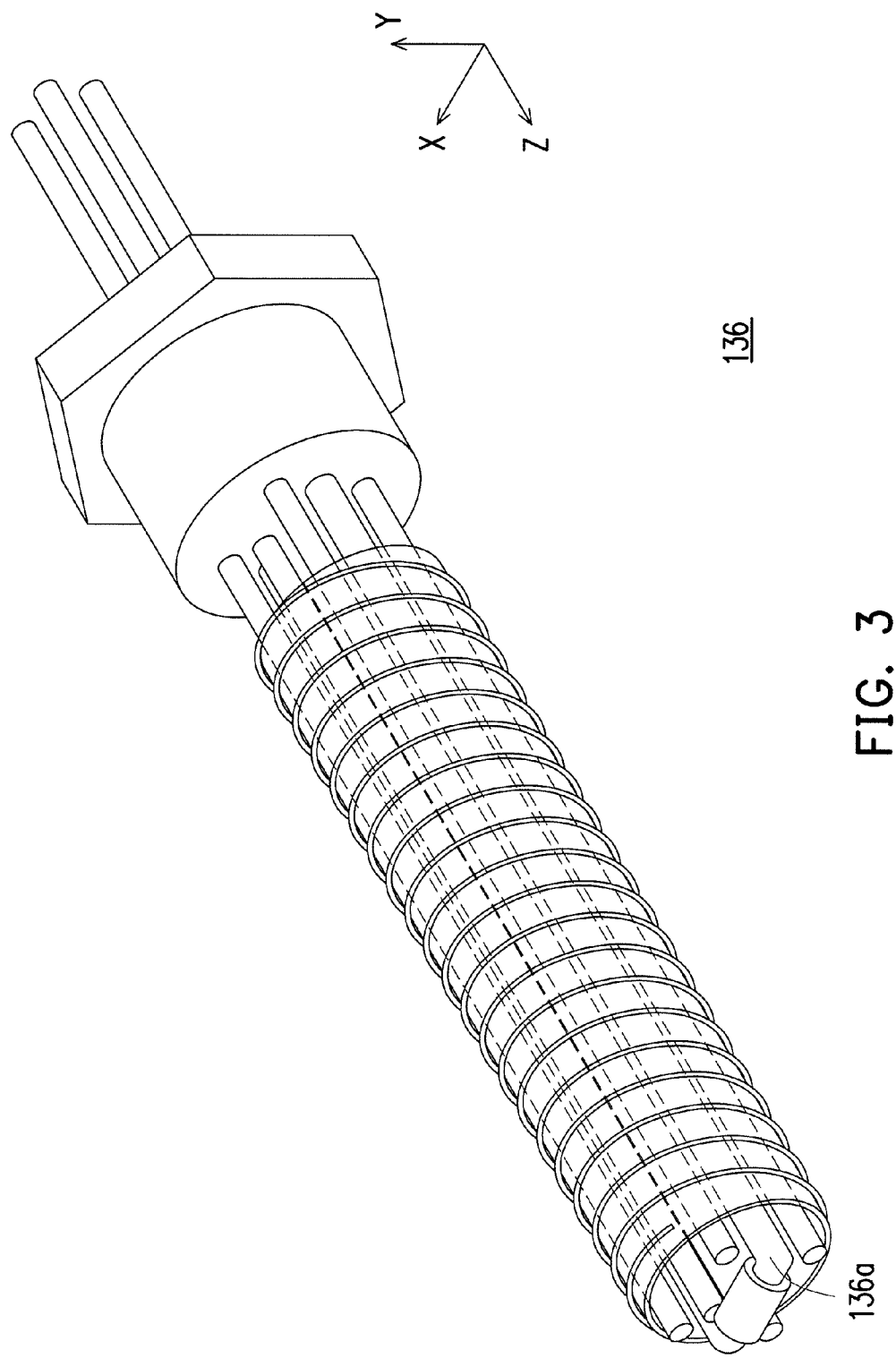
FIG. 3 is a schematic diagram illustrating a pressure sensor in the film thickness monitoring system of FIG. 1.

FIG. 3 is a schematic diagram illustrating a pressure sensor in the film thickness monitoring system of FIG. 1. In the embodiment, the pressure sensor 136 is disposed in the manifold 132. Specifically, the pressure sensor 136 includes a filament 136a disposed in the manifold 132. The pressure sensor 136 is, for example, a Pirani gauge. That is to say, the pressure sensor 136 includes the filament 136a in order to measure the pressure of the manifold 132. In the embodiment, the filament 136a is metal. Specifically, the filament 136a is platinum. However, the metal of the filament 136a may be any suitable metal. Furthermore, the embodiment shows two filaments 136a, but the number of filaments may be one or more, depending on user requirements.

In the embodiment, to measure the pressure of the manifold 132, the filament 136a of the pressure sensor 136 is heated and suspended in a gas in the manifold. That is to say, the filament 136a is disposed in the manifold 132 so as to be exposed to the vaporized deposition material 110a in the manifold 132. In the embodiment, part of the pressure sensor 136 is disposed outside the manifold 132. In other embodiments, the entire pressure sensor 136 is disposed inside the manifold 132. The filament 136a loses heat to the gas as the gas molecules of the vaporized deposition material 110a collide with the filament 136a. If the gas pressure is reduced the number of molecules present will fall proportionately and the filament 136a will lose heat more slowly, and vice versa. Measuring the heat loss is an indirect indication of pressure. In addition, since the manifold 132 is in a vacuum chamber 130, a pressure in the manifold 132 containing the vaporized deposition material 110a is substantially the same as the pressure of the vaporized deposition material 110a at the target 138. Thus, by measuring the pressure of the manifold 132, the deposition rate of the deposition material 110a on the target 138 can be determined.

In the embodiment, the film thickness monitoring system 100 includes the QCM 134 which also measures the deposition rate of the deposition material 110a on the target 138. The QCM 134 measures a mass variation per unit area by measuring the change in frequency of a quartz crystal resonator. The resonance is disturbed by the addition or removal of a small mass due to oxide growth/decay or film deposition at the surface of the acoustic resonator. Thus, the QCM 134 may monitor the rate of deposition of the deposition material 110a on the target 138. Frequency measurements are easily made to high precision. However, the QCM 134 has a relatively short sensor lifetime, and so the film thickness monitoring system 100 does not entirely rely on the QCM 134 for measuring the deposition rate of the deposition material 110a.

In the embodiment, the pressure sensor 136 and the QCM 134 both measure the deposition rate of the deposition material 110a, and the pressure sensor 136 is calibrated to measure the same deposition rate as the measured by the QCM 134. Once the pressure sensor 136 is calibrated, the shutter 134a on the QCM 134 closes so that the deposition material 110a no longer deposits on the QCM 134. Then the film thickness monitoring system 100 continues to measure the deposition rate based on the pressure sensor 136. This way, the QCM 134 may have a longer lifetime as the deposition material 110a is not continually depositing on the QCM 134. Thus, even in a deposition process with a high deposition rate, the QCM 134 may be used for a longer period of time because once the QCM 134 calibrates the pressure sensor 136 the shutter on the QCM 134 closes.

In the embodiment, the pressure sensor 136 has a longer lifetime because the deposition material 110a does not deposit onto the filament 136a because the filament is heated, and has a higher temperature than the vaporized deposition material 110a. However, if parameters change (i.e. temperature, etc.), the deposition rate measured by the pressure sensor 136 may become inaccurate, and the pressure sensor 136 has to be recalibrated by the QCM 134. By having both the pressure sensor 136 and the QCM 134, the film thickness monitoring system 100 may accurately measure the deposition rate for a longer lifetime. The QCM 134 has a longer lifetime and will not need to be replaced as often, reducing costs. In addition, by using both the QCM 134 and the pressure sensor 136, the film thickness monitoring system 100 is able to continuously monitor the film thickness and deposition rate of the deposition material 110a on the target 138. Since the pressure sensor 136 is used as the main sensor to monitor the film thickness and deposition rate of the deposition material 110a on the target 138, the film thickness monitoring system 100 is suitable for deposition processes with high deposition rates. The QCM 134 is used to calibrate the pressure sensor 136, and so even in a deposition process with high deposition rates, the QCM 134 may have a longer lifetime. For example, the film thickness monitoring system 100 is suitable to be applied in the deposition process of organic light emitting diodes, which require high deposition rates. Of course, the film thickness monitoring system 100 may also be applied in other deposition processes with low deposition rates.

Figure 4:
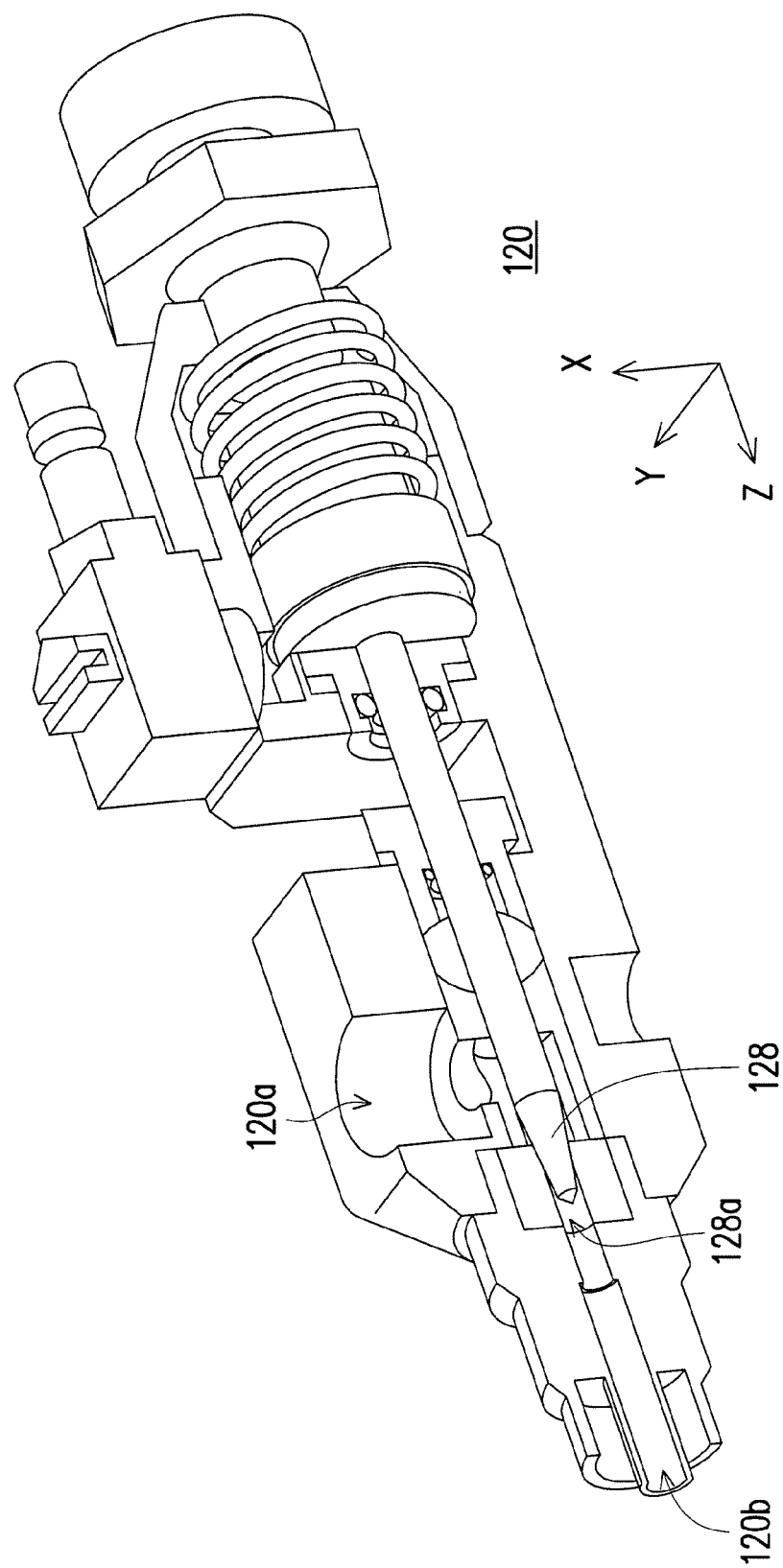
FIG. 4 is a three-dimensional schematic diagram illustrating a cross section of a valve in the film thickness monitoring system of FIG. 1.

FIG. 4 is a three-dimensional schematic diagram illustrating a cross section of a valve in the film thickness monitoring system of FIG. 1. Referring to FIG. 4, the valve 120 includes a first opening 120a and a second opening 120b. The first opening 120a is in communication with the source 110 through the L-pipe 112. The second opening 120b is in communication with the manifold 132 through the transfer tube 122. In the embodiment, the valve 120 is a needle valve. Specifically, the valve 120 further includes a needle 128 and a third opening 128a. The needle 128 is configured to be moved back and forth with respect to the third opening 128a through the valve controller 124. In the embodiment, as seen in FIG. 4, the needle 128 is configured to be moved back and forth in the z-direction. The needle 128 is sloped towards the third opening 128a such that when the needle 128 changes position with respect to the third opening 128a, the size of the third opening 128a changes. This way, the valve controller 124 controlling the position of the needle 128 adjusts the size of the third opening 128a. When the needle 128 is pushed are far as possible into the third opening 128a, the needle 128 blocks the third opening 128a from allowing any fluid to pass through, thereby closing the third opening 128a. When the needle 128 is moved away from the third opening 128a such that there is space between the needle 128 and the walls forming the third opening 128a, fluid may pass through the third opening 128a. Since the needle 128 is sloped, moving the needle 128 back and forth in the z-direction with respect to the third opening 128a adjusts the size of the third opening 128a. If the needle 128 is moved back as far as possible such that the third opening 128a is least possibly obstructed by the needle 128, then the third opening 128a is considered completely open. By adjusting the size of the third opening 128a through the needle 128, the flow rate of the deposition material 110a through the valve 120 is controlled. In other embodiments, the valve 120 is not a needle valve, and is any other suitable valve. That is to say, in other embodiments, other valves that can control and adjust the flow rate of the deposition material 110a flowing through may also be used. In addition, in other embodiments, a valve that does not control and adjust the flow rate of the deposition material 110a is used.

In the embodiment, the film thickness monitoring system 100 is a manufacturing execution system (MES). Specifically, the MES is computerized to track the manufacturing and automate the elements in the film thickness monitoring system 100 to control the entire process. The MES controls the shutter controller 140 and the valve controller 124 to achieve accurate monitoring results and required deposition rates. In addition, the MES controls the temperature of the source 110 as required by the user. Furthermore, the MES determines whether to read the results from the pressure sensor 136 or the QCM 134 as reference for the thickness of the deposition material 110a on the target 138. As a result, the MES allows the film thickness monitoring system 100 to perform, the deposition process accurately and continuously as the entire process is automated.

Figure 5:
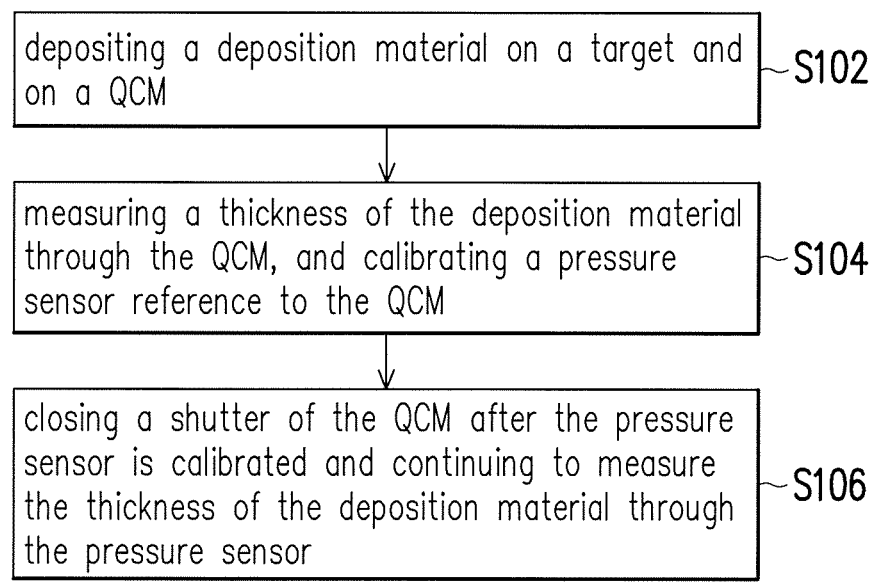
FIG. 5 is a flow chart of a method for monitoring a film thickness deposition process according to an exemplary embodiment.

FIG. 5 is a flow chart of a method for monitoring a film thickness deposition process. The method includes the following steps. The deposition material 110a is deposited on a target 138 through the first nozzles 132a of the manifold 132 and on the QCM 134 through the second nozzle 132b of the manifold 132 (step S102). Prior to step S102, the deposition material 110a in the source 110 is vaporized. In addition, the valve 120 connected to the source 110 and the manifold 132 is opened for the vaporized deposition material 110a to pass through the valve 120 and enter the manifold 132.

Next, a thickness of the deposition material 110a on the target 138 is measured through the QCM 134, and the pressure sensor 136 disposed in the manifold 132 is calibrated to measure the thickness of the deposition material 110a with reference to the QCM 134 (step S104). Specifically, the shutter 134a is opened, and the deposition material 110a deposits on the QCM 134. By depositing the deposition material 110a on the QCM 134, the QCM 134 is able to measure the deposition rate and film thickness of the deposition material 110a on the target 138. At this point, the film thickness monitoring system 100 reads the data from the QCM 134 as reference for the measurements of film thickness and deposition rate. The pressure sensor 136 measures the pressure in the manifold 132, which is substantially the same as the pressure at the target 138. This data from the pressure sensor 136 can determine the deposition rate and the film thickness of the depositor material 110a on the target 138. The pressure sensor 136 is calibrated to measure the deposition rate and film thickness of the deposition material 110a on the target 138 with reference to the QCM 134 due to the high precision of the QCM 134. The steps S102 and S104 may also be performed at the same time. That is to say, the measuring and depositing may be done simultaneously.

Next, the shutter 134a of the QCM 134 facing the second nozzle 132b is closed through the shutter controller 140 after the pressure sensor 136 is calibrated, and the thickness of the deposition material 110a on the target 138 is continued to be measured through the pressure sensor 136 (step S106). Specifically, when the shutter 134a is closed, the deposition material 110a does not deposit onto the QCM 134. By preventing the deposition material 110a from depositing onto the QCM 134, the lifetime of the QCM 134 is lengthened, and cost required for replacing the QCM 134 is reduced. The pressure sensor 136 which has a longer lifetime than the QCM 134 is then used to continue to measure the deposition rate and the film thickness of the deposition material 110a on the target 138. That is to say, the film thickness monitoring system 100 now reads the calibrated pressure sensor 136 as the reference for the deposition rate and the film thickness of the deposition material 110a on the target 138.

Figure 6:
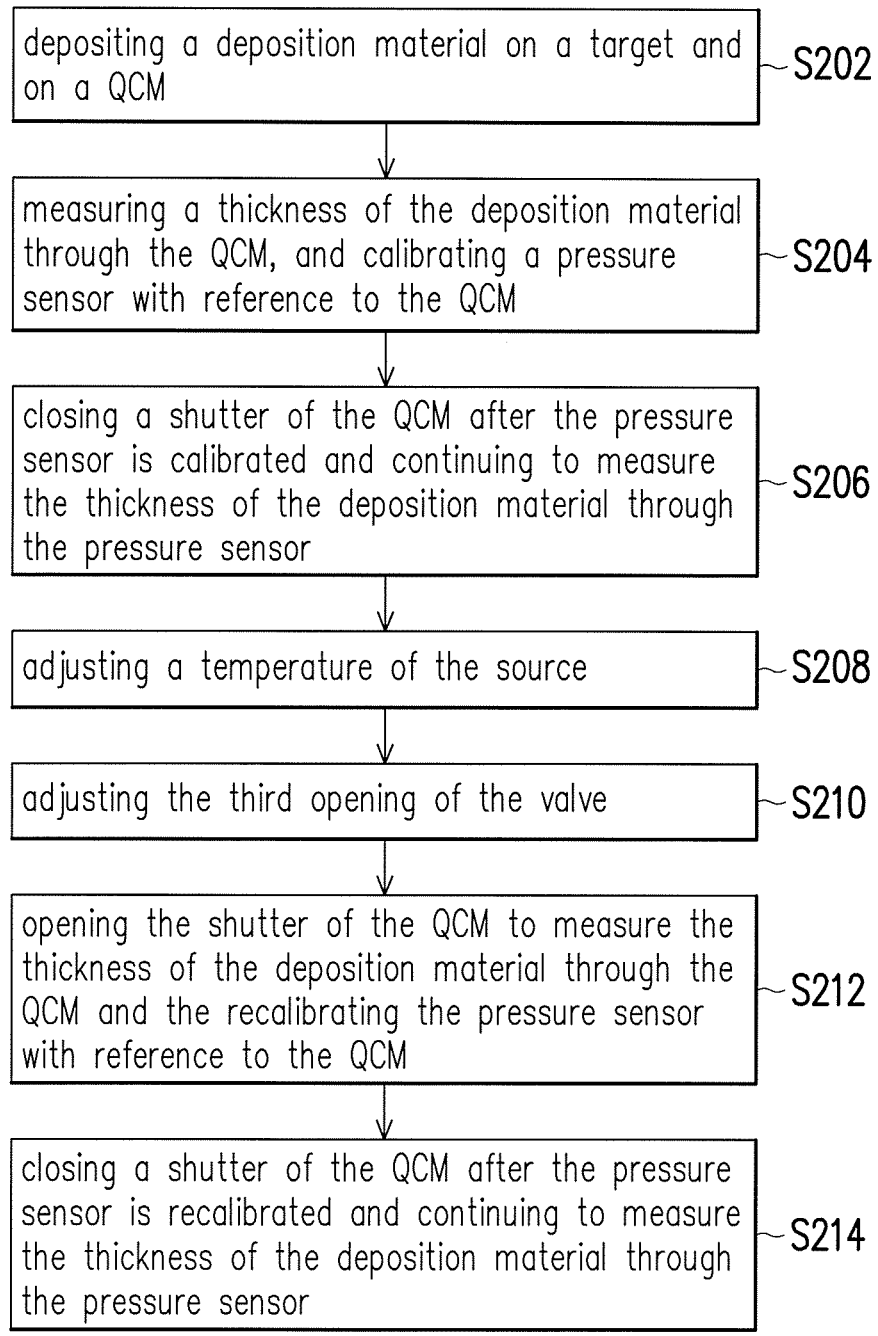
FIG. 6 is a flow chart of a method for monitoring a film thickness deposition process according to another exemplary embodiment.

FIG. 6 is a flow chart of a method for monitoring a film thickness deposition process according to another exemplary embodiment. In the method, the steps S202, S204, and S206 are the same as the steps S102, S104, and S106 in FIG. 5. The same description will not be repeated herein. In the embodiment, the method further includes adjusting a temperature of the source 110 for vaporizing the deposition material 110a (step S208). By adjusting the temperature, the rate in which the vaporized deposition material 110a flowing to and through the valve 120 changes. Changing the rate in which the deposition material 110a is vaporized also changes the rate of deposition. In the embodiment, the rate in which the deposition material 110a is vaporized may be changed due to facilitating the film thickness required. In addition, when the material of the deposition material 110a is changed, the temperature at the source 110 may also be required to change. Different deposition materials 110a require different temperatures to achieve the required deposition rate. In addition, the user may require a different deposition rate for different deposition materials 110a. In some embodiments, the deposition material 110a may be changed from an organic material to an inorganic material, or vice versa. Of course, the disclosure is not limited thereto, and the deposition material 110a may be changed from an organic material to another organic material, or an inorganic material to another inorganic material.

Next, the third opening 128a of the valve 120 is adjusted through the valve controller 124 to control the rate the vaporized deposition material 110a passes through (step S210). Specifically, as described above, the third opening 128a of the valve 120 is adjusted by moving the needle 128. In addition, even though the temperature change at the source adjusts the rate of the vaporized deposition material 110a, the change is not instantaneous to the required rate of deposition. That is to say, to achieve the required deposition rate through change in temperature requires a period of time, whether it is cooling the source 110 or heating the source 110 to the required temperature. Thus, by adjusting the third opening 128a of the valve 120, the rate that the deposition material 110a passes through may be physical controlled. By controlling the rate that the deposition material 110a passes through the valve 120, the rate of deposition is also controlled and adjusted to the required rate. As the temperature changes to the desired temperature at the source 110, the size of the third opening 128a is adjusted at the same time to control the rate of deposition to be at the required rate. This way, the deposition process is continuous.

Next, the shutter 134a of the QCM 134 is opened through the shutter controller 140 to measure the thickness of the deposition material 110a on the target 138 through the QCM 134 and the pressure sensor 136 is recalibrated to measure the thickness of the deposition material 110a with reference to the QCM 134 (step S212). Specifically, when the shutter 134a is opened, the deposition material 110a deposits on the QCM 134. Thereby, the QCM 134 is able to measure the deposition rate and film thickness of the deposition material 110a on the target 138. As mentioned above, since the film thickness and deposition rate are currently monitored (step S206) by the pressure sensor 136, once temperature has changed in step S208, the measurements measured by the pressure sensor 136 may be affected, and the measurements may be inaccurate. Thus, when the temperature has changed, the shutter 134a is opened so that the QCM 134 detects and measures the thickness of the deposition material 110a and the deposition rate. At this point, the film thickness monitoring system 100 reads the data from the QCM 134 as the measurements for film thickness and deposition rate. In the embodiment, the steps S208, S210, and S212 may also be performed at the same time. That is to say, the temperature and the third opening 128a are adjusted at the same time as the shutter 134a is opened and the pressure sensor 136 is being recalibrated.

In the embodiment, the shutter 134a is controlled by the shutter controller 140 to be closed when a size the third opening 128a of the valve 120 is within a first range. When the size of the opening 128a of the valve 120 is outside of the first range, the shutter 134a is controlled to be opened. In the embodiment, the first range of the size of the third opening 128a is 15% to 70% of the third opening 128a completely opened. That is to say, at 100%, the third opening 128a is completely opened, and at 0%, the third opening 128a is completely closed. That is to say, the film thickness monitoring system 100 controls the size of the third opening 128a to achieve the required deposition rate while the temperature at the source is being adjusted. When the size of the third opening 128a is outside of the first range (15% to 70%, for instance), the film thickness monitoring system 100 determines that the parameters changed in the chamber 130 require the pressure sensor 136 to be recalibrated in order to achieve accurate measurements. Similarly, when the size of the third opening 128a is within the first range, the pressure sensor 136 is not required to be recalibrated as the parameters have not changed enough to affect the accuracy of the pressure sensor 136. The first range is not limited to 15% to 70%. The first range may be at any other suitable range as desired by the user for accurate results and an efficient monitoring process. In addition, the third opening 128a is desired to be constant when the temperature and deposition rate are achieved. In some embodiments, when the size of the third opening 128a is outside the first range, the shutter 134a is open, and the shutter controller 140 controls the shutter 134a to close only when the third opening 128a is at the desired constant size. In some embodiments, the third opening 128a is desired to be maintained at around 40% open during the deposition process. Of course, in other embodiments, the size of the third opening 128a that is constant when other parameters (i.e. pressure, temperature, etc.) are fixed may be adjusted as desired by the user.

Next, the shutter 134a is closed after the pressure sensor 136 is recalibrated and the thickness of the deposition material 110a is continued to be measured on the target 138 through the pressure sensor 136 (step S214). As mentioned in the description for step S214, the shutter 134a is closed when the size of the third opening 128a achieves the desired constant size (e.g. 40%). That is to say, the size of the third opening 128a is a factor in the recalibration of the pressure sensor 136. When the shutter 134a is closed, the deposition material 110a does not deposit onto the QCM 134. Once the pressure sensor 136 is recalibrated, the film thickness monitoring system 100 reads the pressure sensor 136 as reference for the thickness of the deposition material 110a on the target 138, and does not use the data from the QCM 134 as reference. The process is continuous, and if the temperature at the source 110 is changed again, the process returns to step S208.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:
1. A film thickness monitoring system, comprising:
a source, configured to provide a deposition material;
a valve, connected to the source; and
a chamber, comprising:
  a manifold, connected to the valve and having at least one first nozzle and at least one second nozzle;
  a quartz crystal microbalance, disposed opposite to the at least one second nozzle, wherein the deposition material is adapted to be deposited on the quartz crystal microbalance through the at least one second nozzle, and the quartz crystal microbalance includes a shutter facing the at least one second nozzle;

a pressure sensor, disposed in the manifold; and a supporter, supporting the quartz crystal microbalance and configured to adjust a position of the quartz crystal microbalance with respect to the at least one second nozzle.

2. The film thickness monitoring system as claimed in claim 1, wherein the chamber further comprises a target, disposed opposite to the at least one first nozzle, wherein the deposition material is adapted to be deposited on the target through the at least one first nozzle.

3. The film thickness monitoring system as claimed in claim 1, wherein the pressure sensor comprises a filament disposed in the manifold.

4. The film thickness monitoring system as claimed in claim 1, wherein the valve is a needle valve.

5. The film thickness monitoring system as claimed in claim 1, further comprising a shutter controller, configured to control the shutter of the quartz crystal microbalance to open or close.

6. The film thickness monitoring system as claimed in claim 1, wherein the source is a crucible adapted to be heated so as to vaporize the deposition material.

7. The film thickness monitoring system as claimed in claim 1, wherein the at least one first nozzle and the at least one second nozzle are disposed on different sides of the manifold.

8. The film thickness monitoring system as claimed in claim 2, wherein a pressure in the manifold is substantially the same as a pressure at the target in the chamber.

9. A chamber adapted for a film thickness monitoring system, comprising:

a manifold, having at least one first nozzle and at least one second nozzle;

a quartz crystal microbalance, disposed opposite to the at least one second nozzle, wherein a deposition material is adapted to be deposited on the quartz crystal microbalance through the at least one second nozzle, and the quartz crystal microbalance includes a shutter facing the at least one second nozzle;

a pressure sensor, disposed in the manifold; and a supporter, supporting the quartz crystal microbalance and configured to adjust a position of the quartz crystal microbalance with respect to the at least one second nozzle.

10. The chamber as claimed in claim 9, further comprising a target, disposed opposite to the at least one first nozzle, wherein the deposition material provided to the manifold is adapted to be deposited on the target through the at least one first nozzle.

11. The chamber as claimed in claim 9, wherein the pressure sensor comprises a filament disposed in the manifold.

12. The chamber as claimed in claim 9, wherein the at least one first nozzle and the at least one second nozzle are disposed on different sides of the manifold.

13. The chamber as claimed in claim 10, wherein a pressure in the manifold is substantially the same as a pressure at the target in the chamber.

* * * * *